United States Patent [19]

Smith et al.

[11] Patent Number: 5,087,559

[45] Date of Patent: Feb. 11, 1992

[54] METHOD OF DETECTING SINGLE BASE SUBSTITUTIONS IN NUCLEIC ACIDS

[75] Inventors: Frances Smith, New York, N.Y.; Peter Palese, Leonia, N.J.

[73] Assignee: Mount Sinai School of Medicine of the City University of New York, New York, N.Y.

[21] Appl. No.: 169,856

[22] Filed: Mar. 18, 1988

[51] Int. Cl.$^5$ .................... C12Q 1/68; C07H 15/12; C12N 15/00

[52] U.S. Cl. ................................ 435/6; 536/27; 935/77; 935/78

[58] Field of Search ................ 435/6; 536/27; 935/77, 935/78

[56] References Cited

OTHER PUBLICATIONS

Molecular Cloning, A Laboratory Manual, Maniatis et al., Cold Spring Harbor Laboratory, 1982, pp. 388–389.
Wetmur et al., Biochemistry, 20, 1981, p. 2999.
Myers et al., Science, 230, 1985, p. 1242.
Smith et al., Virology, 150, 1986, pp. 55–64.
Orosz et al., Biopolymers, (1977), vol. 16, pp. 1183–1188.
Melchior et al., Proc. Nat. Acad. Sci. USA, (1973), vol. 70, 2, pp. 298–302.
Klump, Biochimica et Biophysica Acta, (1977), 475, pp. 605–610.
Britten et al., Cell, (1978), vol. 15, pp. 1175–1186.
Myers et al., Science, (1985), vol. 229, pp. 242–247.
Myers et al., Nucleic Acids Research, (1985), vol. 13, 9, pp. 3111–3129 and 3131–3145.
Myers et al., Letter to Nature, (1985), vol. 313, pp. 495–498.
Fischer et al., Proc. Natl. Acad. Sci. USA, (1983), vol. 80, pp. 1579–1583.
"A Method to Detect and Characterize Point Mutations in Transcribed Genes: Amplification and Overexpression of the Mutant c-Ki-ras Allele in Human Tumor Cells"; Edward Winter et al.; Proc. Natl. Acad. Sci. USA; vol. 82, pp. 7575–7579, Nov. 1975, Biochemistry.
"Detection of Single Base Substitutions by Ribonuclease Cleavage at Mismatches in RNA: DNA Duplexes"; Myers et al.; Science, vol. 230, pp. 1242–1246.
"Evolution of Human Influenza A Viruses over 50 Years: Rapid, Uniform Rate of Change in NS Gene"; Buonagurio et al., Science, (Reprint Series), May 23, 1986, vol. 232, pp. 980–982.
"Measurement of the Mutation Rates of Animal Viruses: Influenza A Virus and Poliovirus Type 1"; Journal of Virology, Aug. 1986, pp. 377–383; Parvin et al.

(List continue on next page.)

Primary Examiner—Robert A. Wax
Assistant Examiner—Mindy B. Fleisher
Attorney, Agent, or Firm—Brumbaugh, Graves, Donohue & Raymond

[57] ABSTRACT

A method for detecting point mutations or base substitutions in a nucleic acid polymer is especially useful for detecting such mutations in the highest melting domain (HMD) of a double-stranded nucleic acid polymer and is particularly suited for use with RNA. The method involves the steps of:

(a) preparing a solution containing a double-stranded nucleic acid polymer comprising a duplex of a single-stranded nucleic acid polymer to be analyzed and a complementary portion of a corresponding wild-type nucleic acid polymer;

(b) placing an aliquot of the solution of the double-stranded nucleic acid polymer into each of a series of containers having a range of denaturing conditions, said series including at least one container in which the denaturing conditions are such that a mismatched nucleic acid duplex having one or more base-pair mismatches within its HMD would be denatured to single-stranded nucleic acid polymers, but in which a perfectly matched nucleic acid duplex having no base-pair mismatches within its HMD would not be so denatured; and (c) comparing the occurrence of single stranded nucleic acids in each container after incubation with a standard.

10 Claims, 4 Drawing Sheets

OTHER PUBLICATIONS

"Denaturation and Renaturation of Penicillium chrysogenum Mycophage Double-Stranded Ribonucleic Acid in Tetraalkylammonium Salt Solutions"; Wetmur et al.; Biochemistry, 1981, vol. 20, pp. 2999-3002.

"Efficient In Vitro Synthesis of Biologically Active RNA and RNA Hybridization Probes from Plasmids Containing a Bacteriophage SP6 Promoter"; Melton et al.; Nucleic Acids Research; vol. 12, No. 18, 1984, pp. 7035-7056.

"Studies on Transformation of *Escherichia coli* with Plasmids"; Douglas Hanahan; Mol. Biol., (1983); vol. 166, pp. 557-580.

"The Mosaic Genome of Warm-Blooded Vertebrates"; Bernardi et al.; Science, vol. 228; pp. 953-958, May, 1985.

"Mismatches in DNA Double Strands; Thermodynamic Parameters and Their Correlation to Repair Efficiences"; Werntges et al.; Science; vol. 14, No. 9, 1986; pp. 3773-3790.

"Nearly All Single Base Substitutions in DNA Fragments Joined to a GC-Clamp can be Detected by Denaturing Gradient Gel Electrophoresis"; Myers et al.; Science, vol. 13, No. 9, 1985.

"Detection of Single Base Substitutions in Influenza Virus RNA Molecules by Denaturing Gradient Gel Electrophoresis of RNA-RNA or DNA-RNA Heteroduplexes"; Smith et al.; Virology, vol. 150, pp. 55-64, (1986).

"Sequence-Determined DNA Separations"; Ann. Rev. Biophys. Bioeng., 1984, vol. 13, pp. 399-423; Lerman et al.

Nucleic Acids Research, vol. 13, 1985, pp. 4811-4820.

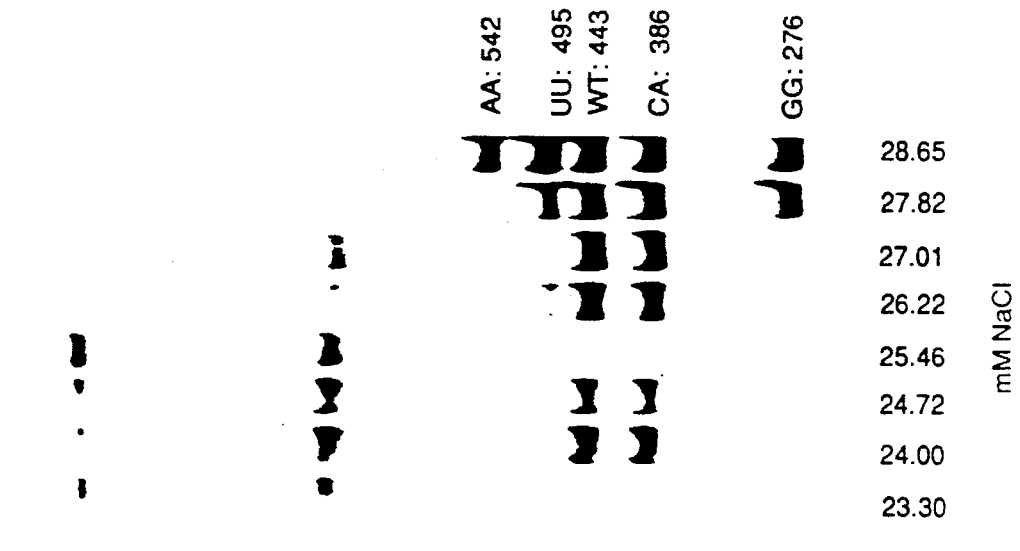
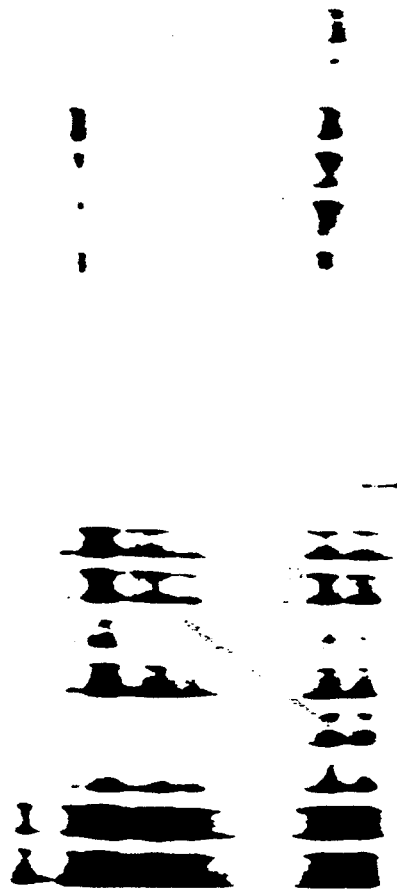
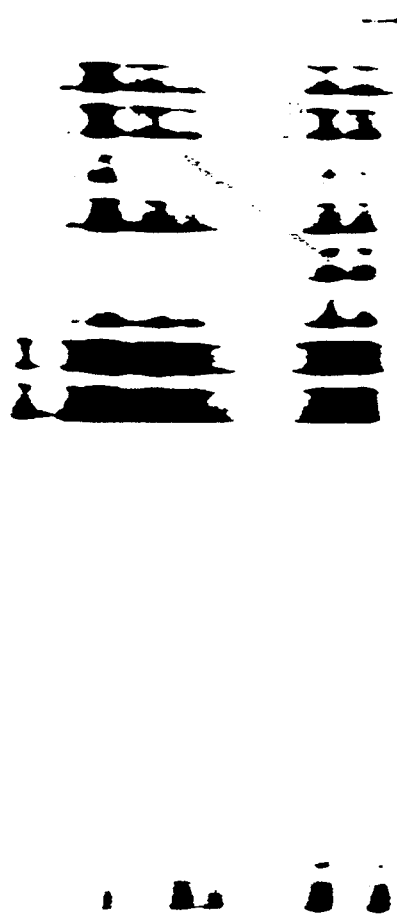

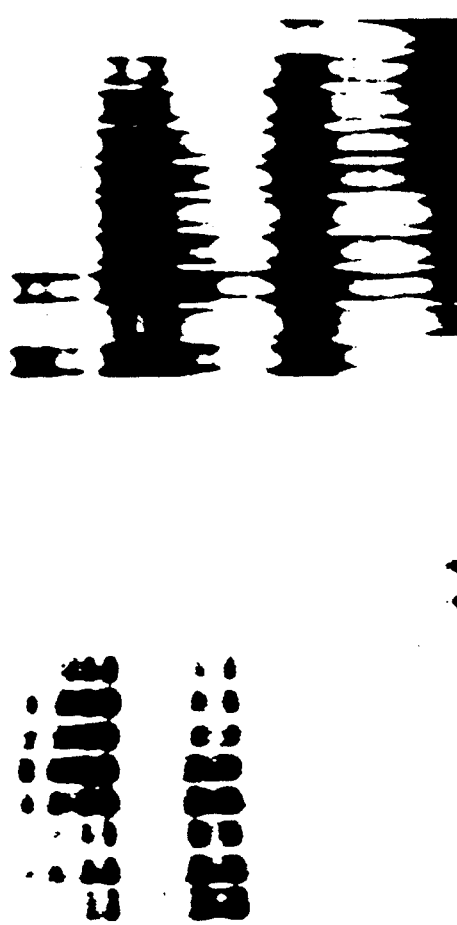

FIG.4
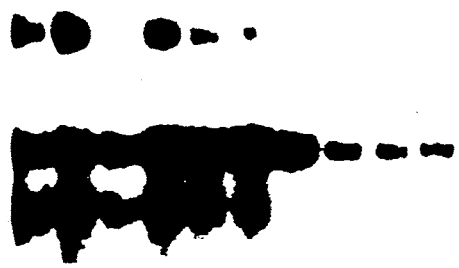
WT: 542
HMD: 443
LMD: 386
20.14 19.55 18.98 18.43 17.90 17.38 16.88 16.39 15.91 15.45 15.00 14.55
% formamide

METHOD OF DETECTING SINGLE BASE SUBSTITUTIONS IN NUCLEIC ACIDS

The invention described and claimed in this application was made with government support under Grant #DK-38381 awarded by the National Institutes of Health. The U.S. government has certain rights in the invention.

BACKGROUND OF THE INVENTION

The present invention relates to a method for readily and reliably detecting single base substitutions in nucleic acid polymers, particularly those substitutions located in the highest melting domain of duplexed nucleic acids.

Melting is defined as the dissociation of the hydrogen bonds that hold double-stranded nucleic acid polymers together. Nucleic acid melting proceeds under equilibrium conditions as a series of relatively abrupt transitions of portions of the polymer (i.e., domains) from helix to random chain. The number of base pairs cooperating to define each domain is determined by the nucleotide sequence. By analysis of the sequence of a DNA molecule, it could be predicted under what conditions the different domains would melt. The lowest melting domain (LMD) comprises those portions of the polymer which melt under the mildest conditions, whereas the highest melting domain (HMD) comprises those that require the most severe conditions to melt.

Denaturing gradient gel electrophoresis for the detection of mutations in DNA molecules was originally developed by Lerman et al., Ann. Rev. Biophys. Bioeng. 13:399–423, 1984. This technique was based on the observation that the electrophoretic mobility of DNA in polyacrylamide gels is sensitive to the secondary structure of the molecule; i.e. helicity, partial melting or complete melting with strand dissociation. Partially melted nucleic acid polymers consisting of double helical regions and disordered single-stranded regions move much more slowly than complete double helixes or completely melted molecules.

The Lerman et al. technique, which makes it possible to resolve complex mixtures of nucleic acid polymers, utilizes a gradient of denaturing solvent in a uniform polyacrylamide gel, run and maintained at the temperature of incipient DNA melting. The solvent gradient provides the equivalent of a shallow linear temperature increase so that dissociation occurs in successively higher melting domains of the DNA.

Recently, further modifications of the Lerman et al. technique have allowed the detection of mutations in genomic RNA of influenza A viruses by analysis of RNA-RNA and RNA-DNA heteroduplexes. See e.g. Smith et al., Virology 150:55–64, 1986. Heteroduplexes were made by hybridizing virion RNA with SP6- or M13-derived cDNA probes of varying length, followed by S1 nuclease digestion to remove unhybridized probe. Duplexes moved through the denaturing acrylamide gel at mobilities determined by molecular weight until they migrated into a denaturant concentration sufficient to melt the duplex. As melting of each domain occurred, the electrophoretic mobility of the fragment abruptly changed. For example, partial strand separation due to melting of low melting domains of a duplex resulted in an abrupt mobility decrease which produced sharp focusing of the bands on the gels. Moreover, differences were observed in melting behavior between perfectly base-pair matched and mismatched low melting domains, that resulted in separation on the gel.

Melting of the highest melting domain (HMD) in a fragment led to strand dissociation, and under these conditions the resolving power of the gel was lost. Accordingly, it was not possible to distinguish perfectly matched from mismatched duplexes if the mismatch occurred within the HMD.

It was recently shown that detection of base substitutions in the higher melting domains of double-stranded DNA (dsDNA) molecules was greatly improved by the addition of a GC-rich nucleotide sequence at one end of the molecule which functioned as a clamp. See, e.g. Myers et al., *Nucleic Acids Res.* 13:3131–3145, 1985. However, the incorporation of a GC clamp requires cloning the sequence to be analyzed. Also, it is not easily applicable to the analysis of mutations in RNA molecules.

It has now been found that base substitutions in the highest melting domain of double-stranded nucleic acid polymers, including DNA-DNA, DNA-RNA and RNA-RNA, can be readily detected using gel electrophoresis by first melting the duplexes in solution and then using the gel system to monitor for strand dissociation.

SUMMARY OF THE INVENTION

The present invention provides a method for detecting point mutations or base substitutions in a nucleic acid polymer. The method is especially useful for detecting such mutations in the highest melting domain (HMD) of a double-stranded nucleic acid polymer and is particularly suited for use with RNA.

The method involves the steps of:

(a) preparing a solution containing a double-stranded nucleic acid polymer comprising a duplex of a single-stranded nucleic acid polymer to be analyzed and a complementary portion of a corresponding wild-type nucleic acid polymer;

(b) placing an aliquot of the solution of the double-stranded nucleic acid polymer into each of a series of containers having a range of denaturing conditions, said series including at least one container in which the denaturing conditions are such that a mismatched nucleic acid duplex having one or more base-pair mismatches within its HMD would be denatured to single-stranded nucleic acid polymers, but in which a perfectly matched nucleic acid duplex having no base-pair mismatches within its HMD would not be so denatured;

(c) allowing the contents of each container to incubate for a period of time sufficient to allow denaturation to occur;

(d) analyzing the contents of each container for the presence of single stranded nucleic acid polymers to determine under which conditions denaturation of the double-stranded nucleic acid polymer occurs; and (e) comparing the results of steps a-d with results for the same method for a corresponding nucleic acid duplex standard perfectly base-pair matched in the HMD, wherein the presence of a point mutation in the HMD is indicated by denaturation of the double-stranded nucleic acid polymer under conditions different from the perfectly basepair matched standard.

A further aspect of the invention involves denaturation of the nucleic acid polymers in solution and monitoring for and analysis of strand dissociation by electrophoresis on a gel, preferably polyacrylamide.

In a still further aspect of the invention, the containers having a range of denaturing conditions are all heated, preferably to about 65° C., and the denaturing conditions are varied by changing the chemical makeup of the solutions within the containers. For example, decreasing concentrations of salt or other stabilizers of the nucleic acid duplex structure or increasing chemical denaturing agent concentrations in the containers will serve to produce increasingly rigorous denaturing conditions.

BRIEF DESCRIPTION OF THE DRAWINGS

FIG. 2 shows detection of single base mutations in in vitro synthesized RNA. FIG. 2A is an autoradiogram of perfectly base-pair matched duplexes of varying lengths; FIG. 2B and FIG. 2C are autoradiograms of duplexes containing single base substitutions and perfectly matched standards.

FIG. 3 shows improved mismatch detection using tetraethylammonium bromide. FIGS. 3A, 3B, and 3C reflect analysis of samples corresponding to those in FIGS. 2A, 2B, and 2C, but using formamide and Et$_4$NBr as the denaturant.

FIG. 4 shows detection of single base mutation in virion genomic RNA.

DESCRIPTION OF THE INVENTION

Figure 1:
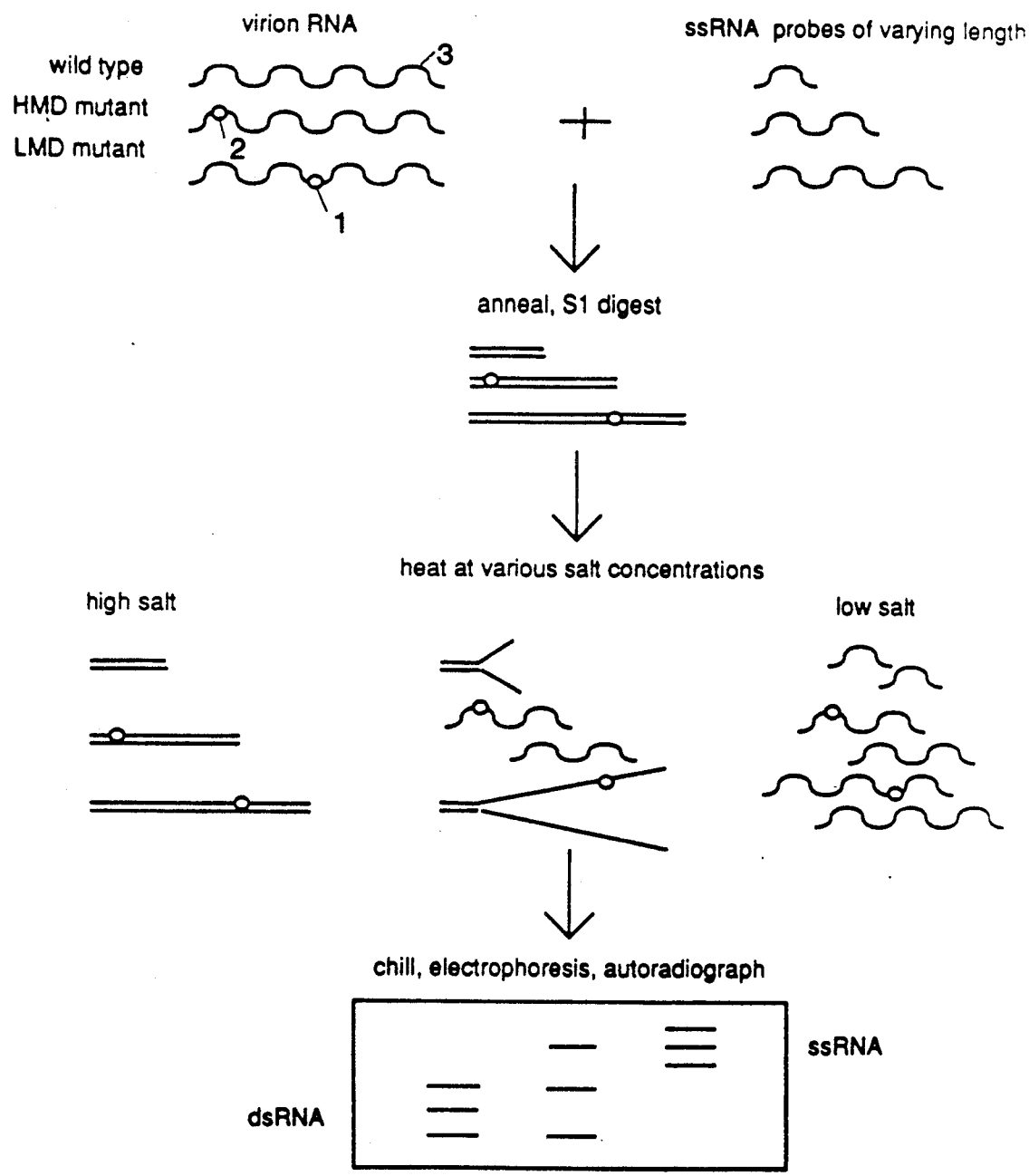
FIG. 1 depicts the experimental scheme according to the solution melting procedure.

FIG. 1 provides a diagrammatic representation of the method of the invention of applied to identification of base substitutions in RNA. As shown in FIG. 1, a labeled single stranded positive sense RNA probe is prepared, for example by transcription in vitro by SP6 polymerase from a dsDNA template that has been linearized by restriction enzymes. These probes are annealed to the negative sense RNA strand to be analyzed which may differ from wild-type RNA by an LMD point mutation 1 or an HMD point mutation 2, or not at all 3. The annealed products are digested with S1 nuclease to remove unreacted probe and to generate a solution containing blunt-ended duplexes. The solution of duplexes is aliquoted into a series of Eppendorf tubes in which the duplexes are exposed to a range of denaturing conditions, for example varying salt or formamide concentration in the tubes or varying the incubation temperatures of the tubes. As shown in FIG. 1, the tubes contain various salt concentrations. Because high ionic strength tends to stabilize the duplexes, high salt (NaCl) concentration prevents dissociation of the duplexes.

After incubation for a period of time sufficient to allow denaturation, if any, to occur, e.g. 15 mins at 65° C., the tubes are rapidly chilled Samples are then fractionated according to size and physical form by gel electrophoresis and detected by using the label on the probe. If the test RNA contains a mutation in the HMD, strand dissociation occurs at a higher salt concentration than is seen for wildtype. Test RNAs that contain mutations in a LMD are not distinguishable from wild-type molecules.

The method depicted in FIG. 1 can be carried out using the same probe to form duplexes with both the nucleic acid polymer to be evaluated and a known wild-type standard, and comparing the conditions under which the resulting duplexes are melted. If the same label is used on the probes for both types of duplexes, however, this approach requires that the sample and the standard be evaluated in parallel tests in different series of containers. While this is certainly feasible, it does introduce the possibility of erroneous results due to the conditions in the sample and standard tubes not being identical. It is therefore preferred to combine the sample and standard in a single series of tubes.

Theoretical calculations and experimental observations of melting properties of double-stranded nucleic acid polymers, i.e., dsDNA, dsRNA and RNA-DNA, have shown that melting proceeds stepwise through a series of discrete domains as the temperature or denaturant concentration used to melt the duplex increases. Because of this, so long as the polymer remains double-stranded applicants postulated that the length of the lower melting domains of a nucleic acid polymer duplex could be varied without affecting the conditions under which ultimate strand dissociation of the duplex into discrete single stranded polymers occurs. It has now been shown that this is in fact the case. A preferred embodiment of the invention takes advantage of this fact and utilizes sample and standard duplex polymers of different lengths in the same tube. As a result, slight fluctuations in temperature or salt concentration between experiments do not adversely affect the results. Differential melting is solely dependent on sequence differences in the HMDs of the sample and standard duplex polymers.

The method of the invention is sensitive enough to detect destabilization of the HMD of a double-stranded nucleic acid polymer, e.g. dsRNA, by a single base mismatch. A NaCl gradient within the range of from 10–40 mM in concentration is effective in resolving 6 of the 8 base-pair mismatches tested. Detection of UG and CA mismatches, however, is not reliable using a NaCl gradient to dissociate the duplex. UG mismatches in dsRNA polymers are believed to be the most stable of mismatches to denaturing conditions. See. e.g. Aboul-Ela et al., Nucleic Acids Res. 13:4811–4824, 1985; Werntges et al., Nucleic Acids Res. 14:3773–3789, 1986. CA mismatches are also believed to be very stable, depending on their nearest neighbors. Aboul-Ela et. al., suora. Both UG and CA mismatches, however, are easily and reliably detected in the presence of tetraethylammonium bromide (Et$_4$NBr) in a final concentration of from 8–250 mM. The reason for this enhanced detection of mismatches is not clear. Nevertheless, Et$_4$NBr, because of its superior ability to resolve base-pair mismatches in the present method, is a preferred denaturing agent.

Other denaturing agents, such as formamide, may also be utilized in the invention, or melting can be caused simply by an increase in temperature. Moreover, the denaturing conditions can be the result of a combination of different agents, for example, formamide plus Et$_4$NBr at elevated temperature. To avoid unnecessary complication of the analysis, however, it is preferred that only a single parameter be varied, e.g. formamide concentration, in the series of containers.

The method provides a means for detecting point mutations in certain domains of double-stranded nucleic acid polymers that heretofore were refractory to such techniques. Thus the method provides a reliable method of detecting point mutations in the HMD of nucleic acid polymers, particularly, but not limited to, RNA, and can clearly resolve mutations located in a virion genomic RNA molecule that were only poorly resolved by previous methods. Use of the present solution melting method in parallel with denaturing gradient gel electrophoresis provides the possibility of detecting all single base mutations in any given DNA or RNA molecule. The number of samples that can be analyzed in each experiment is only limited by the number of molecules of different LMD length that can be resolved by polyacrylamide gel electrophoresis. For example, in a single run, 10 different influenza A NS gene RNAs of different LMD length have been readily distinguished in the same gel by the present method, an analysis of approximately 1500 bases at one time.

The method is useful for analysis of DNA-DNA and RNA-DNA duplexes, as well as RNA-RNA duplexes, enabling the detection of point mutations in DNA molecules. Thus the present method is useful in the screening and characterization of mutations responsible for human genetic diseases (inborn errors of metabolism) at either the RNA or DNA level, as well as the screening of mutations in the DNA or RNA of prokaryotic genomes. The method may be of particular importance in eukaryotic genomic DNA analysis because exons in general show about a 10% higher GC concentration than do introns. See, e.g. Bernardi et al., Science 228:953-58 1985). Since HMD's are also generally GC-rich it is likely. that coding sequences on exons may generally lie in the HMD of any genomic DNA fragment to be analyzed.

EXAMPLE

To demonstrate the effectiveness of the method of the invention for identifying nucleic acid polymers containing single base substitutions in the HMD, eight different mutant forms of the NS gene of influenza A/WSN virus were prepared and compared to a wild-type polymer.

Preparation, Cloning and Mutagenesis of Influenza Viral Genes

The eight different mutant forms of Influenza Viral RNA were prepared as described by Smith et.al., Virology 150:55-64, 1986. The melting map of the NS gene (890 nucleotides in length) which has been published by Smith et al., shows the HMD to be located approximately between bases 100 to 250. Therefore, it was expected that duplexes which include this region should have the same HMD.

Briefly, the formation of the mutants involved cloning a cDNA copy of the NS gene of influenza A/WSN virus into the vectors pGEM3 (pGWNS3) and M13mp18 (M185). The mutant cDNA copies were constructed using the oligonucleotide-directed in vitro mutagenesis system of Amersham, Inc. and obtained therefrom, which is based on the method of Taylor et. al., Nucleic Acids Res. 13:8765-8785, 1985. Phosphorylated oligonucleotides (19 mers, made on a Biosearch oligonucleotide synthesiser) which contained central mutations at positions 171 (A to T) and 175 (T to C or G) in the NS cDNA were annealed with ssDNA derived from M185, and dsDNA was synthesized using the Klenow fragment of E. coli DNA polymerase I in the presence of thio-dCTP. After ligation to produce closed circular DNA and filtration to remove ssDNA, the dsDNA was digested with NciI, which nicks the DNA strand containing dCTP, but not that containing thio-dCTP. Partial digestion with ExoIII removed the wild-type sequence on the nicked strand, and subsequent repolymerization using DNA polymerase I in the presence of dNTPs and ligation produced closed circular dsDNA containing the mutation. TG1 bacterial cells (Amersham) were made competent by the method of Hanahan, J. Molec. Biol. 166:557-580, 1983 and were transformed with this DNA. Phage derived from single plaques were then amplified, and ssDNA was extracted and sequenced using the dideoxy chain termination method as described in the New England Biolabs M13 cloning and sequencing manual.

Approximately 90% of plaques contained the expected mutation. dsDNA was then prepared from bacteria infected with these phage according to standard plasmid purification procedures (See, e.g. Birnboim and Doly, Nucleic Acids Res. 7:1513-1523, 1979) and the cDNA insert was excised and recloned into the RNA transcription vector pIBI31 (pIBI-171T, pIBI-175G, and pIBI-175C). The cDNA insert was then again sequenced, this time using the dideoxy chain terminating method adapted for dsDNA by Chen et al., DNA 4:165-170, 1985, to confirm that the correct insert had been recloned.

Preparation of Nucleic Acid Hybrids

The DNA thus prepared (wild-type or mutagenised plasmid DNA) was digested in a suitable buffer solution with either Rsal, Sau961, BstNl, Hpal, Fokl or Smal to generate templates of differing lengths for positive sense probes complementary to the NS gene, or with HindIII or PstI to generate templates for negative sense probes. DNA templates were then transcribed using SP6, T3, or T7 RNA polymerase in the presence of $[\alpha-^{32}P]CTP$ as described by Melton et.al., Nucleic Acids Res. 12:7035-7056, 1984.

The templates thus prepared were hybridized to each of the mutant viral genes and the wild-type gene to generate AA, GG, CC, UU, GA, CA, UG, and UC mismatched duplexes, or perfectly matched duplexes (see Table I). These duplexes were then treated with S1 nuclease to remove unreacted probe and to generate blunt-ended duplexes according to the Melton et al. protocols. Each of the blunt-ended mutant duplexes had a distinct LMD, by virtue of utilizing probes of different lengths. In addition, 4 perfectly matched duplexes having LMD's of differing lengths were prepared.

TABLE 1

Hybrids used for mismatch detection

| Mismatch | Template* S | AS | Context of sense strand+ |
|---|---|---|---|
| none | wt | wt | GGCAGCACUCUCGGUCUGGAC |
| A:A | wt | 171T | A |
| U:U | 171T | wt | U |
| U:C | wt | 175G | U |
| G:A | 175G | wt | G |
| U:G | wt | 175C | U |
| C:A | 175C | wt | C |
| C:C | 175C | 175G | C |
| G:G | 175G | 175C | G |

*plasmid template used to provide sense (S) or antisense (AS) transcript; wt = wild-type plasmid pGWNS3, 171T = pIBI − 171T, 175C = pIBI − 175C, and 175G = pIBI − 175G +base sequence of sense RNA is given for the wild-type NS gene (from position 165 to 185) of the WSN strain of influenza A virus; sense base at the position of mismatch is indicated for mismatched hybrids

Solution Melting Protocol

The nucleic acid duplexes of different length were mixed together in approximately equal molar ratios, and the volume adjusted such that 2000 TCA-precipitable cpm of each hybrid were added in a volume of 5 μl to several Eppendorf tubes. 10μl of a deionized formamide solution and 5μl of a given salt solution were then added to each tube. Stock salt solutions contained 40 mM Tris pH 7.5, 4 mM EDTA, and either sodium chloride (NaCl 40 mM to 160 mM) or tetraethylammonium bromide (Aldrich, Gold Label; Et$_4$NBr 32 mM to 1M). The actual range of salt concentrations used depended on the batch of hybrids, but up to 20 different tubes were set up in each experiment, with the salt concentration usually increasing by 3% or 20% each step for NaCl or Et$_4$NBr, respectively. In experiments in which the formamide concentration was varied, the final formamide concentration ranged from 35% to 65% or from 15% to 25% for tubes containing 20 mM NaCl or 45 mM Et$_4$NBr, respectively. The tubes containing a total volume of 20 μl were heated at 65° C. for 15 minutes and then chilled quickly on ice. Samples were then loaded onto a 6.5% polyacrylamide gel and electrophoresed at 350 volts for 3.5 hours. Gels were then dried down onto Whatmann 3MM paper and autoradiographed.

(a) Effect of Differing LMD's on Ultimate Dissociation of Perfectly Matched Double-stranded Polymers In devising the preferred method of the invention in which samples and standards are dissociated in a single series of tubes, it was assumed that if the lengths and sequences of the HMDs of the sample and standard were identical, the length of the attached LMD could be varied without affecting strand dissociation. To test this assumption, the perfectly matched RNA-RNA duplexes of varying length described above were heated in solutions containing a constant concentration of formamide (50%) and the varying concentrations of NaCl indicated on FIG. 2A.

FIG. 2A is an autoradiogram showing analysis of a mixture of these perfectly matched duplexes, each of which differs from the others only in the length of their low melting domain. The results depicted in FIG. 2A clearly show that perfectly matched duplexes that differ only in the length of their low melting domains melt at the same salt concentration. In contrast, parallel experiments showed that perfectly matched duplexes having HMDs of different lengths melt differently (data not shown).

(b) Detection of mutations in in vitro transcribed RNA

A single base mismatch is capable of destabilizing a melting domain of a duplex. Previously, however, only single base mutations in low melting domains but not in the HMDs, of duplexes could be detected, as discussed above. The NaCl gradient solution melting method was therefore tested to determine whether it was sensitive enough to detect destabilization in HMD's using the series of the site-specific mutants in the HMD of the NS gene shown in Table I. FIGS. 2B and 2C, show autoradiograms similar to FIG. 2A for dissociation of mixtures of duplexes containing the base-pair mismatches indicated on the figures in 50% formamide and varying salt concentration. As shown in FIGS. 2B and 2C, AA, UU, GG, CC, GA, and UC mismatches were easily detectable in all experiments, whereas UG and AC mismatches resulted in smaller shifts in the NaCl concentration required for strand dissociation and in some experiments were not detected.

(c) Improved detection of mismatches by using Et$_4$NBr

Tetraalkylammonium salts have been shown to have a destabilizing effect on both dsDNA and dsRNA molecules and at high concentrations eliminate base composition effects on the helix-coil transition (See, e.g. Melchior and von Hippel, Proc. Natl. Acad. Sci. 70:298–302, 1973; Wetmur et.al., Biochemistry 20:2999–3002, 1981). Because Et$_4$NBr interacts so differently from the way NaCl interacts with RNA duplexes, it was of interest to determine whether the substitution of Et$_4$NBr for NaCl in the solution melting method would have any effect on the efficiency of mutation detection. Two types of experiments were performed. First, the concentration of Et$_4$NBr was kept constant at 45 mM and the concentration of formamide was varied between 15% and 25%. The results in FIG. 3 show that UG and CA mismatches were now easily and reproducibly resolved from wild-type duplexes, with no loss of resolution in the detection of the other mismatches. The melting conditions shown in FIG. 3 were similar to those for FIG. 2 with the exception that 45 mM Et$_4$NBr and varying formamide concentrations as indicated were used. In a second experiment, the concentration of formamide was held constant at 17.5% while the final concentration of Et$_4$NBr in the tubes was varied from 8 mM to 250 mM. Again, all mutations were easily detectable (data not shown).

(d) Detection of a single base mutation in viral RNA

The Et$_4$NBr formamide denaturant solutions were used to screen a group of influenza A/WSN virus mutants containing known mutations shown by Parvin et al., J. Virol, 59:377–383, 1986, to be scattered throughout the length of their NS gene. Virion RNA was hybridized as described above with RNA probes of varying length, and after S1 nuclease treatment the resulting blunt-ended hybrids were mixed with wild-type controls and analyzed using a formamide gradient at a fixed concentration of Et$_4$NBr (45 mM). FIG. 4 shows that mutations affecting LMDs gave melting patterns indistinguishable from that of the wild-type virus, whereas the virion RNA that contained a mutation in its HMD was clearly distinguishable. With reference to FIG. 4, the HMD mutant contains a mutation at position 169 which results in a GA mismatch; the LMD mutant contains a mutation at position 72 that results in a UG mismatch. The unlabelled negative sense RNA used for hybridization has been purified from various mutant virus stocks as described by Smith et al., Virology 150:55–64, 1986. Therefore, this method gives clear, easily interpretable results with mutations in an uncloned virion RNA which had been only poorly resolved by denaturing gradient gel electrophoresis (Smith et al., 1986), and was not detectable by RNAase A cleavage analysis (data not shown).

The foregoing examples make use of radioactive labels on the probes to provide for detection of the nucleic acids following electrophoresis. Other labelling methods, including fluorescent or chromogenic labels, could also be used.

We claim:

1. A method of detecting point mutations in the highest melting domain of a nucleic acid polymer, comprising:

(a) preparing a solution containing a double-stranded nucleic acid polymer comprising a duplex of a single-stranded nucleic acid polymer to be analyzed and a complementary portion of a corresponding wild-type nucleic acid polymer;

(b) placing an aliquot of the solution of the double-stranded nucleic acid polymer into each of a series of containers having a range of denaturing conditions, said series including at least one container in which the denaturing conditions are such that a nucleic acid duplex having one or more base-pair mismatches within its highest melting domain would be denatured to single-stranded nucleic acid polymers, but in which a nucleic acid duplex having no basepair mismatches within its highest melting domain would not be so denatured;

(c) allowing the contents of each container to incubate for a period of time sufficient to allow denaturation to occur;

(d) analyzing the contents of each container for the presence of single stranded nucleic acid polymers to determine under which conditions denaturation of the double-stranded nucleic acid polymer occurs; and (e) comparing the results of steps a-d with results for the same method for a corresponding nucleic acid duplex standard perfectly base-pair matched in the highest melting domain, wherein the presence of a point mutation in the highest melting domain is indicated by denaturation of the double-stranded nucleic acid polymer under conditions different from the perfectly base-pair matched standard.

2. A method according to claim 1, wherein the double-stranded nucleic acid polymer to be analyzed and the perfectly matched standard are simultaneously incubated in the same containers.

3. A method according to claim 2, wherein the double-stranded nucleic acid polymer and the perfectly base-pair matched duplex standard have low melting domains of different lengths.

4. A method according to claim 1, wherein the range of denaturing conditions in the containers is provided by varying a single parameter selected from among the reaction temperature of the container, the concentration of a chemical denaturing agent within the container, and the concentration of a stabilizing agent within the container.

5. A method according to claim 4, wherein the single parameter varied is the concentration of a chemical denaturing agent.

6. A method according to claim 5, wherein the chemical denaturing agent is formamide.

7. A method according to claim 4, wherein the single parameter varied is the concentration of a chemical stabilizing agent.

8. A method according to claim 7, wherein the chemical stabilizing agent is sodium chloride 9. A method according to claim 1, wherein the double-stranded nucleic acid polymer to be analyzed and the perfectly matched standard comprise a labeling moiety selected from among radioactive labels, fluorescent labels, and chromogenic labels.

10. A method according to claim 9, wherein the labeling moiety is a radioactive label.

* * * * *